United States Patent
Na et al.

(10) Patent No.: US 10,531,980 B2
(45) Date of Patent: Jan. 14, 2020

(54) PORTABLE ELECTRONIC MOXIBUSTION THERAPY DEVICE

(71) Applicants: DONGSHIN UNIVERSITY INDUSTRY-ACADEMY COOPERATION, Naju-shi, Jeollanam-do (KR); STORYTECH, INC., Seoul (KR)

(72) Inventors: Chang Su Na, Naju-si (KR); Jung Chul Lee, Gwangju (KR); Min Woo Cheon, Gwangju (KR); Dae Hwan Youn, Gwangju (KR); Ki Won Nam, Gwangju (KR); Young Eok Kim, Gwangju (KR); Jung Bin Bae, Gyeonggi-do (KR)

(73) Assignees: DONGSHIN UNIVERSITY INDUSTRY-ACADEMY COOPERATION, Naju-si, Jeollanam-do (KR); STORYTECH, INC., Seoul (KR)

( * ) Notice: Subject to any disclaimer, the term of this patent is extended or adjusted under 35 U.S.C. 154(b) by 656 days.

(21) Appl. No.: 15/312,417

(22) PCT Filed: May 19, 2014

(86) PCT No.: PCT/KR2014/004467
§ 371 (c)(1),
(2) Date: Nov. 18, 2016

(87) PCT Pub. No.: WO2015/178513
PCT Pub. Date: Nov. 26, 2015

(65) Prior Publication Data
US 2017/0087005 A1   Mar. 30, 2017

(51) Int. Cl.
A61F 7/00 (2006.01)
A61H 39/06 (2006.01)
A61F 7/02 (2006.01)

(52) U.S. Cl.
CPC ............... *A61F 7/007* (2013.01); *A61F 7/02* (2013.01); *A61H 39/06* (2013.01);
(Continued)

(58) Field of Classification Search
CPC  A61F 7/007; A61F 7/02; A61H 39/06; A61H 2201/5082; A61H 2201/5007; A61H 2201/102; A61H 2201/0157
See application file for complete search history.

(56) References Cited

FOREIGN PATENT DOCUMENTS

JP   2010-207302 A   9/2010
JP   2011-010701 A   1/2011
(Continued)

*Primary Examiner* — Kaitlyn E Smith
*Assistant Examiner* — Yasamin Ekrami
(74) *Attorney, Agent, or Firm* — Bret E. Field; Bozicevic, Field & Francis LLP

(57) ABSTRACT

Disclosed is a portable electronic moxibustion therapy device which can be conveniently carried after being charged by a user to provide the effects of conventional moxibustion treatment anywhere and anytime, and which can maximize the effects of moxibustion treatment by directly applying heat stimulation while being near but not in direct contact with an acupuncture point to be treated and simultaneously providing an indirect thermal effect continuously to the surrounding area and the area around the acupuncture point to be treated. The portable electronic moxibustion therapy device according to the present invention comprises: an upper main body including a battery and a control circuit unit provided therein, and separate the skin from the bottom end of the funnel portion.

22 Claims, 6 Drawing Sheets

(52) U.S. Cl.
CPC .......... *A61F 2007/0078* (2013.01); *A61F 2007/0096* (2013.01); *A61F 2007/0207* (2013.01); *A61F 2007/0226* (2013.01)

(56) References Cited

FOREIGN PATENT DOCUMENTS

| | | |
|---|---|---|
| KR | 10-0320034 B1 | 12/2001 |
| KR | 10-2001-0020953 A | 1/2002 |
| KR | 10-0572706 B1 | 4/2006 |
| KR | 10-2006-0085703 A | 7/2006 |
| KR | 10-2009-0069220 A | 6/2009 |
| KR | 10-2010-0128631 A | 12/2010 |
| KR | 20-2011-0007331 U | 7/2011 |

[Fig. 1]
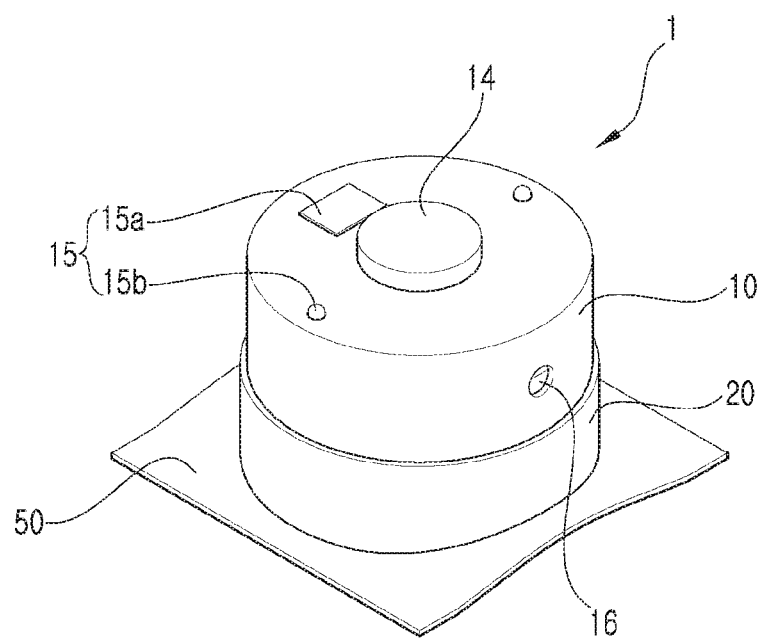

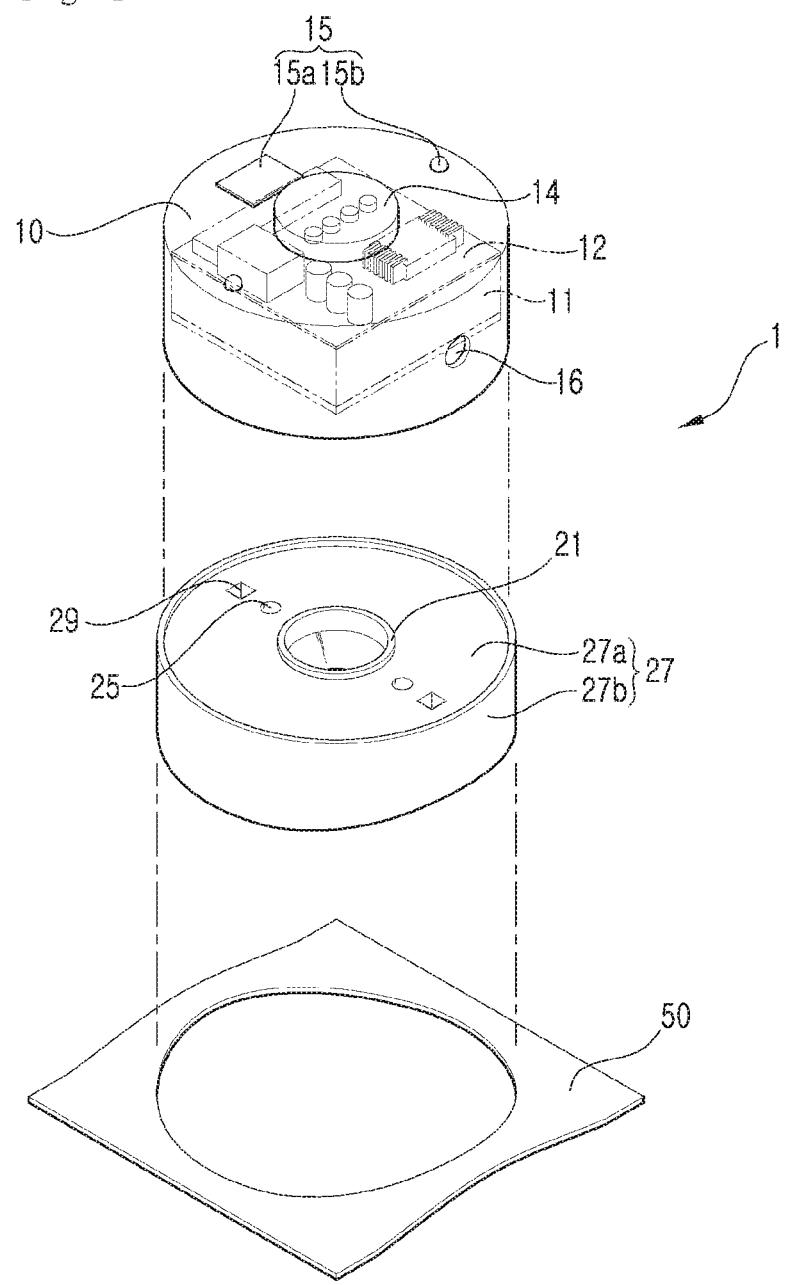
[Fig. 2]

[Fig. 3]
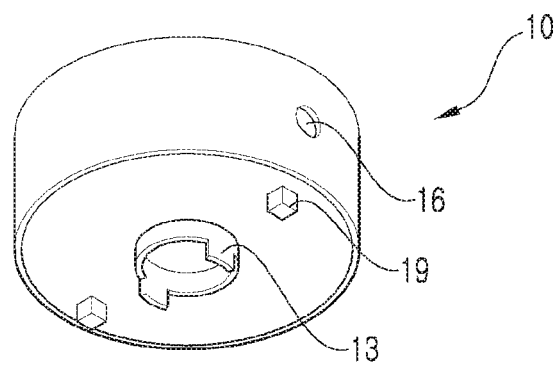
[Fig. 4]
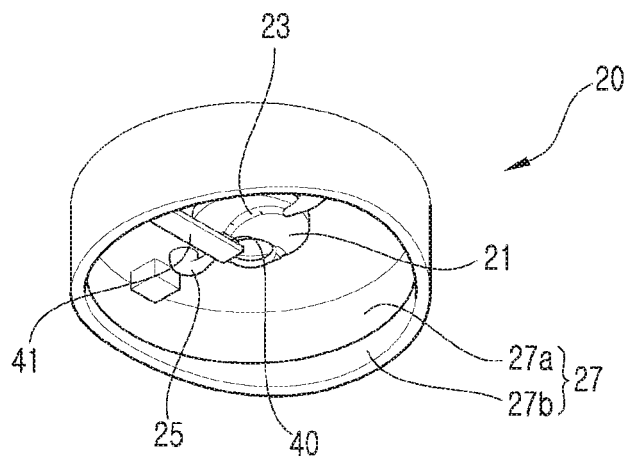

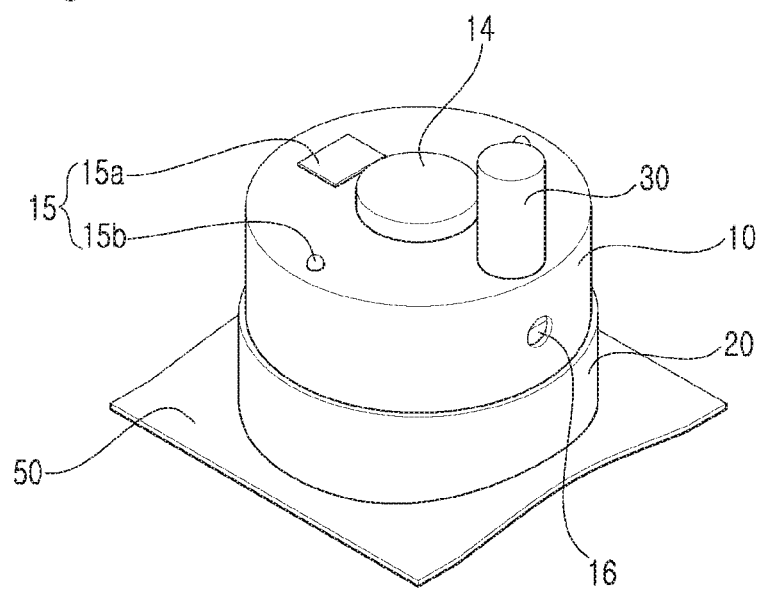
[Fig. 5]

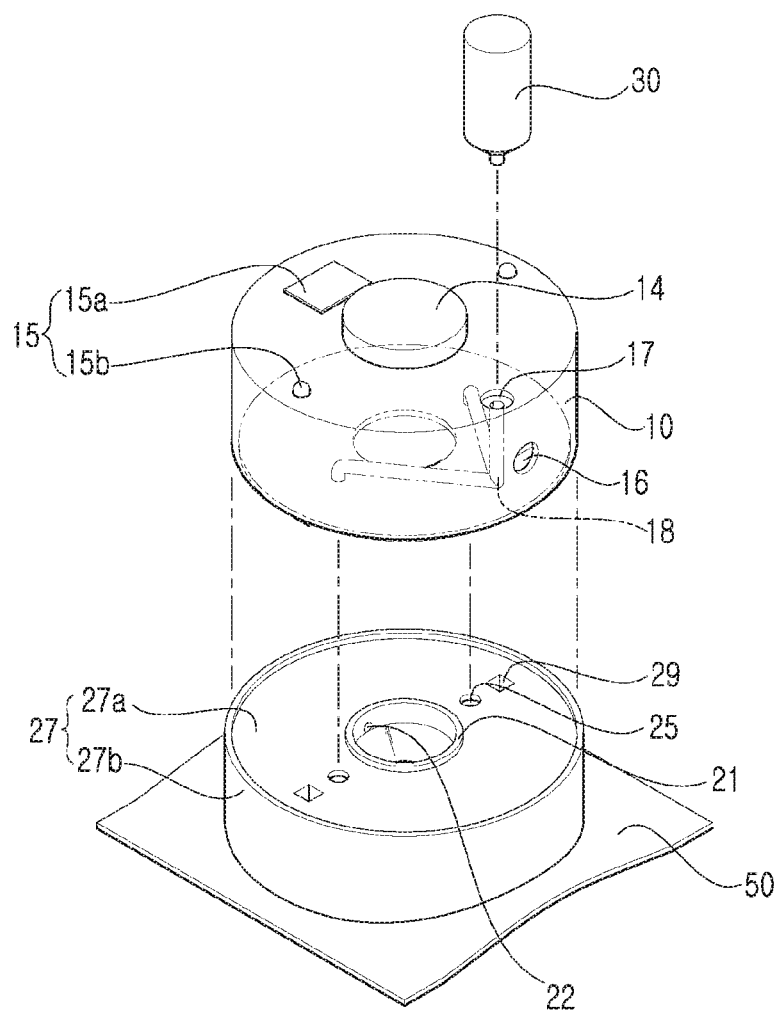
[Fig. 6]

[Fig. 7]
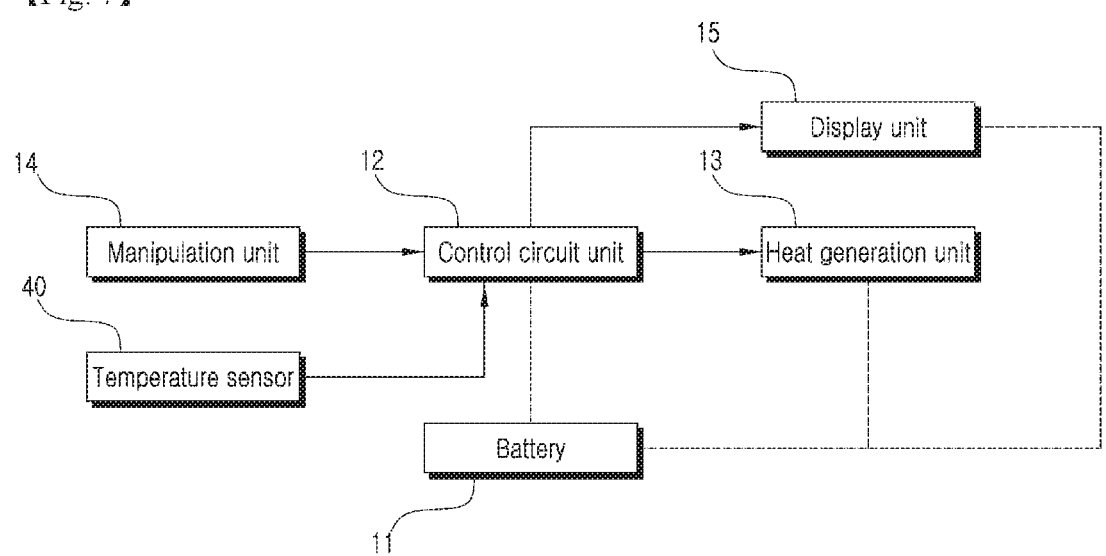

PORTABLE ELECTRONIC MOXIBUSTION THERAPY DEVICE

CROSS-REFERENCE TO RELATED APPLICATION

This Application is a Section 371 National Stage Application of International Application No. PCT/KR2014/004467, filed May 19, 2014, the contents of which is hereby incorporated by reference in its entirety.

TECHNICAL FIELD

The present invention relates to a portable electronic moxibustion therapy device, which allows a user to have a traditional moxibustion therapy effect while the user conveniently carries the moxibustion therapy device after it is charged and, more particularly, to a portable electronic moxibustion therapy device, which can maximize a moxibustion therapy effect and enables, for example, moxa extracts or a moxibustion liquid including the moxa extracts to penetrate the skin through a liquefaction state and a vaporization type wet contact so that a pharmacological action is performed by intensively applying a heat stimulus to a corresponding acupuncture point to be treated in a close state without having a direct contact with the corresponding acupuncture point while applying an indirect thermal effect to surrounding acupuncture points and portions near the corresponding acupuncture point and simultaneously controlling a heat stimulus temperature and a heat stimulus time.

BACKGROUND ART

In general, in the acupuncture and moxibustion treatment of oriental medicine, a needle or moxibustion is used as means for stimulating spots on the body suitable for acupuncture. From among them, moxibustion is widely used because the public can perform a treatment relatively easily using the moxibustion and the moxibustion has no side effects compared to the needle and the moxibustion is widely used at homes for health management.

In an herbal medicine, moxibustion functions to treat or prevent a disease by stimulating spots on the body suitable for acupuncture, meridian system, and an aching part of the human body by applying heat to them, and includes various types. A mugwort moxibustion treatment using mugwort is used most widely.

A mugwort moxibustion treatment method using mugwort is divided into an indirect moxibustion method and a direct moxibustion method depending on a thermal transfer method. It has been known that when conventional mugwort moxibustion treatment is performed, the size of a bundle of mugwort to be ignited is appropriate to be a size half one grain of rice to one grain of rice. In the conventional mugwort moxibustion treatment, a heat stimulus is applied for a proper time by controlling the burning time while generating the proper amount of heat capable of maximizing a therapy effect attributable to mugwort moxibustion while preventing a burn attributable to mugwort moxibustion.

In the conventional mugwort moxibustion treatment method, if the size of a mugwort bundle is small, there are problems in that the handling of the mugwort bundle is very difficult and a sufficient therapy effect cannot be obtained because the amount of heat generated is too small. In contrast, if the size of a mugwort bundle is too large, there are problems in that a scar, such as a spot, is generated at a treatment position due to a burn attributable to the excessive amount of heat generated and in particular, ash remaining after mugwort is burn flies.

In the conventional mugwort moxibustion treatment method, the indirect moxibustion method includes a method for raising a large mugwort pole on yellow soil in which salt, a garlic, and water are mixed at a treatment portion and indirectly delivering a heat stimulus to the treatment portion by burning the large mugwort pole. This method has several problems, such as that this method is inconvenient and a thermal transfer effect is not uniform.

Furthermore, in the conventional mugwort moxibustion treatment method, smoke is generated when a mugwort bundle is burnt, a mugwort bundle has to be ignited whenever treatment is performed, and there is a danger of suffering burns because the mugwort bundle falls during treatment.

A modernized mugwort moxibustion treatment device of a direct moxibustion method, which is now on the market, has a hollow cylinder or hollow multilateral cylinder shape, and has been improved to have a structure in which smoke generated therein comes down to a lower treatment portion to deliver heat and a thin resin material protection film including adhesives is included on a skin contact portion. However, there are problems in that there still remains a danger of a burn, a large blister attributable to burns remains at a corresponding portion after treatment and there is a danger of secondary bacillus infection, and it is difficult and inconvenient to handle ash because a large amount of ash remains after being burnt.

In the case of the indirect moxibustion method which is used by sticking mugwort moxibustion into a hemispherical assistant device having a plurality of holes formed therein, there are problems in that it is very inconvenient because several pieces of mugwort moxibustion have to be burnt, there is a great danger of a burn, a person may suffer a serious burn at another portion if the assistant device falls upon treatment, and it is difficult to handle ash because a large amount of ash is generated.

Accordingly, there is an increasing interest in the development of a moxibustion treatment device capable of reducing such inconvenience and problems, of being easily carried by each person and of continuing to stimulate spots on the body suitable for acupuncture anywhere and at any time. In line with such a tendency, a plurality of portable moxibustion treatment devices has been developed. However, the conventional portable moxibustion treatment device has a problem in that sufficient heat is not applied to the skin or there is a danger of a burn attributable to overheating because a process of bringing a portion (contact portion) through which heat is applied to the skin into contact with the skin or detaching the portion from the skin is performed by experiences and an operator's determination. Furthermore, the conventional portable moxibustion treatment device has problems in that a variety of types of treatment according to symptoms are impossible because the moxibustion treatment device is limited to a heat transfer method for consistently transferring heat simply as disclosed in Korean Patent Application Publication No. 10-2006-0085703 (Jul. 28, 2006), a far-infrared radiation heating method using a light source as disclosed in Korean Patent No. 10-0572706 (Apr. 13, 2006), and a burning heating method using the burning of a mugwort as disclosed in Korean Patent No. 10-0320034 (Dec. 24, 2001) and Korean Patent Application Publication No. 10-2010-0128631 (Dec. 8, 2010) and in view of treatment effects, the moxibustion treatment device is not practically applied to a specialized medical institution because it does not have the same effect as the moxibustion treatment of a specialized medical institution.

DISCLOSURE

Technical Problem

An object of the present invention is to provide a portable electronic moxibustion therapy device, which allows a user to have a traditional moxibustion therapy effect without any time and place limits while the user conveniently carries the moxibustion therapy device after it is charged.

Another object of the present invention is to provide a portable electronic moxibustion therapy device, which can maximize a moxibustion therapy effect by intensively applying a heat stimulus to a corresponding acupuncture point to be treated in a close state without having a direct contact with the corresponding acupuncture point and simultaneously continuously applying an indirect thermal effect to surrounding acupuncture points and portions around the corresponding acupuncture point.

Yet another object of the present invention is to provide a portable electronic moxibustion therapy device, which enables, for example, moxa extracts or a moxibustion liquid including the moxa extracts to penetrate the skin through a liquefaction state and a vaporization type wet contact so that a pharmacological action.

Still another object of the present invention is to provide a portable electronic moxibustion therapy device, which can be effectively used depending on symptoms in specialized medical institutions in addition to by common users because a heat stimulus temperature and a heat stimulus time are standardized and provided so that the moxibustion therapy device can be generalized as a medical instrument and a heat stimulus temperature is selected for each step, if necessary, and used for treatment.

Technical Solution

An object of the present invention is achieved by a portable electronic moxibustion therapy device, including an upper main body in which a battery and a control circuit unit are provided on the upper side of the main body, a heat generation unit for generating heat under the control of the control circuit unit is protruded from the upper main body at the bottom of the upper main body, and a manipulation unit and a display unit are provided on the outer surface of the main body; and a lower base which is coupled to the bottom of the upper main body, has the heat generation unit inserted into the center of the lower base and coupled to the lower base, and includes a funnel portion which concentrates heat transferred from the heat generation unit on one point at the bottom of the funnel portion and has a guide groove formed along the outer circumference surface of the funnel portion, a moxibustion liquid injection pipe which is provided outside the funnel portion and injects a moxibustion liquid so that the moxibustion liquid is vaporized along the guide groove, and a skin contact portion which is provided on the outer circumference surface of the lower base, forms an indirect heating space by surrounding the funnel portion, and isolates the bottom of the funnel portion from a skin.

In accordance with a preferred characteristic of the present invention, a coupling protrusion is protruded and formed on the bottom surface of the upper main body, and a coupling groove to which the coupling protrusion is detachably coupled is formed on the top surface of the lower base.

In accordance with a preferred characteristic of the present invention, a charging jack connection hole to which the charging jack of a charging cable for charging the battery is connected is provided on one side of the upper main body.

In accordance with a preferred characteristic of the present invention, the moxibustion liquid is manually injected through the moxibustion liquid injection pipe.

In accordance with a preferred characteristic of the present invention, a cartridge coupling hole communicating with the moxibustion liquid injection pipe by a connection pipe is formed on the top surface of the upper main body so that the moxibustion liquid is automatically injected into the moxibustion liquid injection pipe. A moxibustion liquid cartridge filled with the moxibustion liquid is detachably coupled to the cartridge coupling hole.

In accordance with a preferred characteristic of the present invention, the moxibustion liquid includes moxa extracts.

In accordance with a further preferred characteristic of the present invention, the moxibustion liquid includes 100 parts by weight of moxa extracts and 1 to 10 parts by weight of a microbial cultivated liquid cultivated using one or more of yeast fungus, lactobacilli, photosynthesis bacteria, aspergilli, and actinomicetes ray fungi using a liquid state medium at room temperature.

In accordance with a further preferred characteristic of the present invention, the moxibustion liquid includes 100 parts by weight of moxa extracts and 1 to 40 parts by weight of additional extracts including at least one selected from a group consisting of bitter gourd extracts, dandelion extracts, pine needle extracts, *Curcuma longa* L. extracts, *Cirsium japonicum* extracts, and *Plantago asiatica* extracts.

In accordance with a further preferred characteristic of the present invention, the moxibustion liquid includes 100 parts by weight of moxa extracts, 1 to 40 parts by weight of additional extracts including at least one selected from a group consisting of bitter gourd extracts, dandelion extracts, pine needle extracts, *Curcuma longa* L. extracts, *Cirsium japonicum* extracts and a *Plantago asiatica* extracts, and 1 to 10 parts by weight of a microbial cultivated liquid cultivated using one or more of yeast fungus, lactobacilli, photosynthesis bacteria, aspergilli, and actinomicetes ray fungi using a liquid state medium at room temperature.

In accordance with a preferred characteristic of the present invention, two guide grooves are formed. The two guide grooves start from both sides on the upper part of the funnel portion, downward make a turn around the outer circumference surface of the funnel portion by 360 degrees, and reach the bottom of the funnel portion. Two moxibustion liquid injection pipes are formed and connected to the tops of the guide grooves, respectively.

In accordance with a preferred characteristic of the present invention, a heat dissipation hole is formed to penetrate the funnel portion.

In accordance with a preferred characteristic of the present invention, a temperature sensor for measuring a temperature of a portion to be treated and transferring the measured temperature to the control circuit unit is provided at the bottom of the funnel portion.

In accordance with a preferred characteristic of the present invention, the temperature sensor includes a resistance temperature detector (RTD).

In accordance with a further preferred characteristic of the present invention, the resistance temperature detector is made of one of platinum, nickel, copper, an iron-nickel alloy, a copper-nickel alloy, and a copper-iron alloy.

In accordance with a preferred characteristic of the present invention, a temperature of a portion to be treated according to heat generated from the heat generation unit of the upper main body is set to one of a first step having a temperature range of 40 to 45° C., a second step having a temperature range of 45 to 50° C., and a third step having a temperature range of 50 to 60° C. in response to a manipulation of the manipulation unit.

In accordance with a preferred characteristic of the present invention, the temperature sensor is located on the end of a support horizontally extended from a middle location with respect to the skin under the funnel portion. The end of the support on which the temperature sensor is located is spaced 1 to 5 mm from the lower center of the funnel portion to an outside.

In accordance with a preferred characteristic of the present invention, the skin contact portion of the lower base includes an inner container forming the indirect heating space by surrounding the funnel portion and the outer container surrounding the inner container and made of a heat-resistant rubber material, wherein the outer container is more extended to upper and lower sides than the inner container and has a bottom actually come into contact with the skin.

In accordance with a further preferred characteristic of the present invention, the outer container has a cylinder form. Locations portions of 0° and 180° and location portions 90° and 270° at the bottom corner of the outer container are formed to have a smooth curve having a height difference of 2 mm so that a contact force with the skin is improved and the bottom corner rarely slides.

In accordance with a further preferred characteristic of the present invention, the outer container includes 1 to 25 parts by weight of a far-infrared emission device selected from the group consisting of 100 parts by weight of a heat-resistant rubber, sericite, illite, mica, and white mica.

In accordance with a more preferred characteristic of the present invention, the amount of 15 to 25 parts by weight of the far-infrared emission device is mixed with 100 parts by weight of the heat-resistant rubber.

The portable electronic moxibustion therapy device in accordance with a preferred characteristic of the present invention further includes an adhesive pad coupled to a lower circumference of the lower base and directly attached to the skin, for attaching the lower base to surrounding portions of the skin of a portion to be treated.

Advantageous Effects

In accordance with the portable electronic moxibustion therapy device according to the present invention, there are excellent effects in that a user can conveniently carry the portable electronic moxibustion therapy device after it is charged and can attach it to a corresponding acupuncture point without any time and place limits, thus having a traditional moxibustion therapy effect and the portable electronic moxibustion therapy device can also be easily used in a medical institution.

Furthermore, in accordance with the portable electronic moxibustion therapy device according to the present invention, there are excellent effects in that a moxibustion therapy effect can be maximized because a heat stimulus is directly applied to a corresponding acupuncture point to be treated intensively in a close state by means of the funnel portion that concentrates heat on the corresponding acupuncture point without having a direct contact with the corresponding acupuncture point and at the same time, an indirect thermal effect continues to be applied to a surrounding acupuncture point and portions around the corresponding acupuncture point to by means of the heat dissipation hole of the funnel portion and the skin contact portion and a moxibustion therapy effect can be maximized because moxa extracts or a moxibustion liquid including the moxa extracts penetrate the skin through a liquefaction state and a vaporization method wet type contact, thus maximizing a pharmacological action.

Furthermore, there are excellent effects in that the portable electronic moxibustion therapy device according to the present invention can be generalized as a medical instrument because a heat stimulus temperature and a heat stimulus time can be standardized and provided and the portable electronic moxibustion therapy device can be effectively used depending on symptoms in a specialized medical institution as well as by a common user because it is configured to select a heat stimulus temperature for each step, if necessary, and to perform treatment.

Furthermore, in accordance with the portable electronic moxibustion therapy device according to the present invention, the upper main body including a simple circuit and the lower base in which a moxibustion liquid is vaporized are separated, and the portable electronic moxibustion therapy device is configured so that a moxibustion liquid of a liquid state is injected according to an automatic injection method using the cartridge or an external manual injection method using a spuit. In particular, the popularization of the portable electronic moxibustion therapy device can be accelerated because the external manual injection method can be fabricated and sold at a low price, and medical expenses can be significantly reduced if anyone can easily use the portable electronic moxibustion therapy device through such popularization.

DESCRIPTION OF DRAWINGS

FIG. 1 is a perspective view of a portable electronic moxibustion therapy device according to an embodiment of the present invention.

FIG. 2 is an exploded perspective view of the portable electronic moxibustion therapy device according to an embodiment of the present invention.

FIG. 3 is a bottom perspective view of an upper main body in the portable electronic moxibustion therapy device according to an embodiment of the present invention.

FIG. 4 is a bottom perspective view of a lower base in the portable electronic moxibustion therapy device according to an embodiment of the present invention.

FIG. 5 is a perspective view of the portable electronic moxibustion therapy device including a moxibustion liquid cartridge according to an embodiment of the present invention.

FIG. 6 is a partial exploded perspective view of the portable electronic moxibustion therapy device including a moxibustion liquid cartridge according to an embodiment of the present invention.

FIG. 7 is a block diagram of the portable electronic moxibustion therapy device according to an embodiment of the present invention.

MODE FOR INVENTION

Preferred embodiments of the present invention will now be described in detail with reference to the accompanying drawings, but the embodiments are intended to describe the present invention in detail to the extent that those skilled in the art to which the present invention pertains may readily practice the present invention. This does not mean that the technical spirit and category of the present invention are restricted by the embodiments.

A portable electronic moxibustion therapy device 1 according to an embodiment of the present invention allows a user to have a traditional moxibustion therapy effect without any time and place limits while the user conveniently carries the moxibustion therapy device after it is charged and also maximizes a moxibustion therapy effect by intensively applying a heat stimulus to a corresponding acupuncture point to be treated in a close state without having a direct contact with the corresponding acupuncture point and simultaneously continuously applying an indirect thermal effect to surrounding acupuncture points and portions around the corresponding acupuncture point. As shown in FIGS. 1 to 7, the portable electronic moxibustion therapy device 1 includes an upper main body 10 in which a battery 11 and a control circuit unit 12 are provided on the upper side of the main body, a heat generation unit 13 for generating heat under the control of the control circuit unit 12 is protruded from the main body at the bottom thereof, and a manipulation unit 14 and a display unit 15 are provided on the outer surface of the main body; and a lower base 20 which is coupled to the bottom of the upper main body 10, has the heat generation unit 13 inserted into the center of the lower base and coupled to the lower base, and includes a funnel portion which concentrates heat transferred from the heat generation unit 13 on one point at the bottom of the funnel portion and has a guide groove 23 formed along the outer circumference surface of the funnel portion, a moxibustion liquid injection pipe 25 which is provided outside the funnel portion 21 and injects a moxibustion liquid so that the moxibustion liquid is vaporized along the guide groove 23, and a skin contact portion 27 which is provided on the outer circumference surface of the lower base, forms an indirect heating space by surrounding the funnel portion 21, and isolates the bottom of the funnel portion 21 from the skin.

In this case, the upper main body 10 functions to provide heat to the funnel portion 21 of the lower base 20 by generating the heat for vaporizing a moxibustion liquid. The upper main body 10 includes the battery 11 provided within the upper main body 10, for generating heat from the heat generation unit 13 and supplying power for driving the control circuit unit 12 and the display unit 15, the control circuit unit 12 provided within the upper main body 10, for controlling whether or not to generate heat from the heat generation unit 13 and the operation of the display unit 15 in response to a manipulation of the manipulation unit 14 or a sensor signal from a temperature sensor 40 to be described later, the heat generation unit 13 formed at the bottom of the upper main body 10 and protruded therefrom, for generating heat in response to power supplied from the battery 11 under the control of the control circuit unit 12, the manipulation unit 14 provided on the outer surface of the upper main body 10, for providing a manipulation signal to the control circuit unit 12, and the display unit 15 for displaying the current operating state, operating time, etc. of the portable electronic moxibustion therapy device 1 according to an embodiment of the present invention.

The battery 11 supplies power for the operation of the elements of the upper main body 10, and is formed of a rechargeable battery. In this case, a charging jack connection hole 16 to which the charging jack (not shown) of a charging cable for charging the battery 11 is connected is provided on one side of the upper main body 10. In an embodiment, the battery 11 may have a replaceable battery form.

The control circuit unit 12 generates a control signal for controlling whether or not to generate heat from the heat generation unit 13 and the operation of the display unit 15 in response to a manipulation of the manipulation unit 14 or a sensor signal from the temperature sensor 40 to be described later. The control circuit unit 12 is formed of a printed circuit board designed according to a control algorithm for the precondition operation of the portable electronic moxibustion therapy device 1 according to an embodiment of the present invention.

The heat generation unit 13 generates heat in response to power supplied from the battery 11 under the control of the control circuit unit 12 and transfers the heat for evaporating a moxibustion liquid to the funnel portion 21 of the lower base 20 to be described later. The heat generation unit 13 is protruded toward the center of the upper main body at the bottom thereof. Although not shown, the heat generation unit 13 is made of a metallic body having a hot wire whose generation of heat is controlled by an ON-OFF-controlled or pulse width modulation method of a known chopper method embedded therein.

The manipulation unit 14 allows a user or operator to select whether or not to drive the portable electronic moxibustion therapy device 1 according to an embodiment of the present invention or operation mode through his or her manipulation. The manipulation unit 14 is installed on the outer surface, in particular, at the top surface of the upper main body 10, and may have various forms, such as a switch, a knob or an operation dial.

The display unit 15 may include a liquid crystal display 15*a* for displaying a timer time according to the operation of the portable electronic moxibustion therapy device 1 according to an embodiment of the present invention or a temperature of a portion to be treated, which is measured by the temperature sensor 40 to be described later, and a combination of a variety of types of LEDs 15*b* for displaying whether heat is generated from the heat generation unit 13 and the charging and discharging state of the battery 11.

The lower base 20 is coupled to the bottom of the aforementioned upper main body 10. The lower base 20 provides a moxibustion treatment effect to a corresponding acupuncture point to be treated and portions around the corresponding acupuncture by vaporizing a moxibustion liquid using heat transferred from the heat generation unit 13 of the upper main body 10 in the state in which the lower base 20 has been brought in contact with the skin. The lower base 20 includes the funnel portion 21 having the heat generation unit 13 inserted at the center thereof, for concentrating heat from the heat generation unit 13 on one point at the bottom of the funnel portion 21 and for having the guide groove 23 that vaporizes a moxibustion liquid so that the moxibustion liquid flows down formed along the outer circumference surface of the funnel portion 21, the moxibustion liquid injection pipe 25 provided outside the funnel portion 21, for injecting a moxibustion liquid to be provided to the guide groove 23, and the skin contact portion 27 provided on the outer circumference surface of the lower base 20, for forming an indirect heating space for providing a heating effect around an acupuncture point to be treated by surrounding the funnel portion 21 and isolating the bottom of the funnel portion 21 from the skin.

The funnel portion 21 has a shape narrowed toward the bottom, and functions to maximize a moxibustion therapy effect by concentrating heat from the heat generation unit 13 on a portion right on a corresponding acupuncture point to be treated and also to provide a heating effect to portions around the corresponding acupuncture point by transferring the heat to an indirect heating space formed by the skin contact portion 27. The funnel portion 21 is fabricated using a metallic body having excellent thermal conductivity.

Furthermore, a heat dissipation hole 22 is formed at the upper part of the funnel portion 21 to penetrate the funnel portion 21. The heat dissipation hole 22 provides a heating effect to portions around a corresponding acupuncture point to be treated by discharging some of heat within the funnel portion 21 to the indirect heating space formed by the skin contact portion 27. One or a plurality of the heat dissipation holes 22 may be spaced apart from each other and formed at the upper part of the funnel portion 21.

The guide groove 23 is formed on the outer circumference surface of the funnel portion 21. The guide groove 23 is adapted to vaporize a moxibustion liquid injected through the moxibustion liquid injection pipe 25 in a dripping manner while the moxibustion liquid flows down inside the guide groove 23. Two guide grooves 23 are formed on the outer circumference surface of the funnel portion 21. The two guide grooves 23 start from both sides on the upper part of the funnel portion 21, downward make a turn around the outer circumference surface of the funnel portion 21 by 360 degrees, and reach the bottom of the funnel portion 21. In some embodiments, only one guide groove 23 may be formed on the outer circumference surface of the funnel portion 21.

The moxibustion liquid injection pipe 25 is provided outside the funnel portion 21. The moxibustion liquid injection pipe 25 is adapted to inject a moxibustion liquid to be provided to the guide groove 23. The number of moxibustion liquid injection pipes 25 corresponds to the number of guide grooves 23. The bottoms of the moxibustion liquid injection pipes 25 are inward curved and coupled to the tops of the guide grooves 23, respectively.

A moxibustion liquid may be injected manually through the moxibustion liquid injection pipe 25, that is, in a dripping manner through a spuit, etc. In some embodiments, as shown in FIGS. 5 and 6, a moxibustion liquid may be automatically injected by a moxibustion liquid cartridge 30 coupled to the upper main body. If a moxibustion liquid is automatically injected by the moxibustion liquid cartridge 30, a cartridge coupling hole 17 to which the moxibustion liquid cartridge 30 is detachably coupled is formed to penetrate the upper main body 10 on the top surface thereof. Furthermore, the cartridge coupling hole 17 communicates with the moxibustion liquid injection pipe 25 of the lower base 20 by the connection pipe 18, and thus a moxibustion liquid within the moxibustion liquid cartridge 30 is automatically injected into the moxibustion liquid injection pipe 25 of the lower base 20. A connection pipe 18 is formed in a branch pipe form that connects the cartridge coupling hole 17 and a plurality of the moxibustion liquid injection pipes 25.

A moxibustion liquid manually injected through the moxibustion liquid injection pipe 25 or charged in the moxibustion liquid cartridge 30 may include only moxa extracts, may include herbal medicine mixture extracts including 100 parts by weight of moxa extracts and 1 to 10 parts by weight of a microbial cultivated liquid cultivated using one or more of yeast fungus, lactobacilli, photosynthesis bacteria, aspergilli, and actinomicetes ray fungi using a liquid state medium at room temperature, may include herbal medicine mixture extracts including 100 parts by weight of moxa extracts and 1 to 40 parts by weight of additional extracts including at least one selected from the group consisting of bitter gourd extracts, dandelion extracts, pine needle extracts, *Curcuma longa* L. extracts, *Cirsium japonicum* extracts, and *Plantago asiatica* extracts, or may include herbal medicine mixture extracts including 100 parts by weight of moxa extracts, 1 to 40 parts by weight of additional extracts including at least one selected from the group consisting of bitter gourd extracts, dandelion extracts, pine needle extracts, *Curcuma longa* L. extracts, *Cirsium japonicum* extracts and a *Plantago asiatica* extracts, and 1 to parts by weight of a microbial cultivated liquid cultivated using one or more of yeast fungus, lactobacilli, photosynthesis bacteria, aspergilli, and actinomicetes ray fungi using a liquid state medium at room temperature.

A mugwort is a perennial herbaceous plant belonging to asteraceae. Young leaves of a mugwort are used for edibility, and leaves and stems thereof are used for medicinal use. Moxa produced from a grown mugwort like cotton of rhubarb color is used for moxibustion mugwort. It has been known that a mugwort prevents a thrombus because it contains cineol. In particular, it has been known that artemisiacapillaris makes warm the stomach and intestines and the hand and feet, improves a liver function, and has an excellent detoxification action and antibacteria action because it contains vitamin $A_1$ (radical reform and aging suppression), $B_1$, $B_2$ and C, calcium, and iron content. In an herbal medicine, it has been known that a mugwort has stanching, lifeblood, recovery-of-gash, wind cold, antibacteria, anti-inflammation, alleviation-of-pain and deodorization actions. A mugwort has an herb medicine name of an "artemisia herb" and includes about 30 kinds. A mugwort is a perennial herb belonging to asteraceae and has been traditionally used for edibility and medicinal use in various ways. In general, a smooth and young mugwort is called "lavandulaefolia" or "artemisia dubia wall", and a mugwort dried and used for medicines or mugwort moxibustion is called "moxa." The chlorophy of a mugwort functions to prevent cancer and purity blood and performs hematogenous and sterilization functions, a function of extending a microvessel, a function of accelerating metabolism, and an antiallergic action. Aging is performed in a process of producing lipoperoxide through a combination of a large amount of unsaturated fatty acid within the human body and oxygen within blood under the influence of radioactive rays or ultraviolet rays. The tannin component of a mugwort prevents the aging of a cell by strongly suppressing the generation of lipoperoxide. A mugwort has a unique roaring scent and functions to remove chill and refuse harmful insects. Furthermore, a mugwort includes abundant nutrition components for activating the liver function and abundant vitamin and mineral and thus performs fatigue recovery and physical strength improvement functions by making smooth the detoxification function of the liver and lipometabolism. The blood circulation function of a mugwort improves the circulation of the blood of gastric mucosa. High quality of the fibroid material of a mugwort helps eloquence by making smooth the peristaltic motion and secretion of mucus of the intestines. Furthermore, a mugwort has special effects in a variety of types of women diseases by solving waist and shoulder pains, that is, chronics of women, and chill and moisture, purifies blood, controls blood pressure by reducing a cholesterol number within blood, and has an effect in fatness by helping lipometabolism. Furthermore, a mugwort includes abundant chlorophy and vegetable fibers for an anticancer action and abundant mineral and vitamin, and thus has a strong detoxification action for discharging toxins to the outside of the body by decomposing the toxins, such as a variety of types of medicines, fertilizer, and agricultural pesticides. The major components of major bioactive substances according to the present invention contributes the circulation of the blood, strengthens a detoxification action and a human body immunity function, and performs a variety of types of useful biological active actions through a combination with other bioactive substances.

A bitter gourd is a bine annual plant of a dicotyledon cucurbitales cucurbitaceae called a balsam pear, and is chiefly distributed to Asia tropics. A flower is yellow, and a stem is a tendril and winds up another thing. A young fruit and testa are edible, and a seed is used for medicinal use. A bitter gourd includes a vegetable insulin component (polypeptide P) that helps the burning of grape sugar and lowers blood sugar by preventing grape sugar from being synthesized again within the body, charantin that is a fat-solubility component making active the function of a pancreas that secretes insulin, a protein component (called Momordica Anti-HIV Protein (MAP30) that suppresses the reproduction of an HIV virus, vitamin C of 120 mg contained in a total amount of 100 g, beta carotin that switches to vitamin A, and minerals, such as iron and potassium. A bitter gourd has medical effects, such as anti-inflamatory, antitoxic, detoxification, sterilization, and lifeblood. Furthermore, a bitter gourd contains polypepide components, such as protein, in addition to vitamin C that is not broken by heat, and contains anti-inflamatory, antitoxic, detoxification, and sterilization components. Bitter gourd extractions are added to herbal medicine mixture extracts corresponding to a moxibustion liquid, thus strengthening the human body immunity function and performing detoxification and a variety of types of useful biological active actions.

Dandelion, *Taraxacum platycarpum* is a many-years herb belonging to asteraceae and distributed to the entire Korea areas, and is a plant the entire plant body of which, such as roots, leaves and flower are edible. From old times, in an herbal medicine, it has been said that the leaves of dandelion removes fever and has an anti-inflamatory effect. Accordingly, the leaves of dandelion have been used to treat diseases, such as cystitis, vaginitis, gastritis, a gastric ulcer, a duodenal ulcer, duodenitis, and arthritis accompanied by heat and an inflammation. In an herbal medicine, a plant body prior to the blooming of a flower is used as pharmaceuticals called a taraxacum herb. Such a taraxacum herb has effects in a swelling, mastitis, a sore throat, appendicitis, peritonitis, acute hepatitis, and jaundice attributable to heat, and is also used a symptom that prevents urine due to heat. In particular, the linoleic acid and choline component of dandelion has an effect in geriatric diseases, such as high blood pressure, a heart disease, and epilepsy, and is used as pharmaceuticals for choleresis acceleration and antirheumatic. Furthermore, it has been reported that dandelion extractions and components separated from dandelion are used to improve microbes within the useful intestines of the large intestine, blood sugar, and a plasma lipids profile, to perform an anticancer effect and a therapy effect for changing the pipes of stomach and intestines and for enhancing an amorphous cell, and to perform an anti-virus action. Dandelion extractions are added to herbal medicine mixture extracts corresponding to a moxibustion liquid, thus enhancing the human body immunity function and performing an anti-inflamatory action and a variety of types of useful biological active actions.

*Curcuma longa* L. is an annual plant belonging to zingiberaceae and has the origin of the product of tropical Asia. *Curcuma longa* L. is cultivated in areas other than the southern area of China and the mountainous areas of Korea. The root and trunk of *Curcuma longa* L. are used as herb medicine materials, and *Curcuma longa* L. contains known components, such as turmerone, zingerene, phellandrene, 1,8-cineole, borneol, and dehydroturmerone, and contains arabinose, fruit sugar, glucose, starch, and organic acids. The root of *Curcuma longa* L. contains diketone compound curcumin, that is, a yellow crystalline component, and yellow pigments including p-hydroxycinnamoylferuloylmethane and p,p'-dihydroxydicinnamoylmethane of about 0.3%, that is, the derivatives of diketone compound curcumin. In addition, *Curcuma longa* L. contains an essential oil of 1~5%, non-volatile oil of about 2.4%, starch of 50%, crude fiber of 5%, ash of 4%, and moisture of about 16%. *Curcuma longa* L. functions to accelerate blood circulation, and is used as medicines for a bruise or extravasated blood in addition to shoulder arthralgia. *Curcuma longa* L. also has an action for lowering cholesterol within blood for suppressing virus within the liver. *Curcuma longa* L. has a variety of types of biological effects for preventing antioxidation, anticancer, antimutagenic, anti-inflamatory, and imbecility, protecting the liver function, suppressing disorder, and reducing cholesterol. In particular, *Curcuma longa* L. has an excellent anticancer effect and functions to prevent a variety of types of cancer. *Curcuma longa* L. extractions are added to herbal medicine mixture extracts corresponding to a moxibustion liquid, and thus enhance the human body immunity function and perform an anti-inflamatory action and a variety of types of useful biological active actions.

A pine needle is a leaf of *Pinus densiflora* Seibold et Zuccarini. A *Pinus densiflora* Seibold et Zuccarini is an evergreen needleaf tree that grows wild in all of the mountains of Korea. Red pines chiefly growing in land areas occupy a major part of the *Pinus densiflora* Seibold et Zuccarini, and include a Korean nut pine, a *Pinus ridiga* Mill, a Japanese black pine (black pine), and a white pine. A pine needle, that is, a leaf of *Pinus densiflora* Seibold et Zuccarini, is used for medicinal use of the herbal medicine or folk remedies or healthy food from old times. In accordance with Donguibogam, it has been known that a pine needle has treatment effects in a gastroenteric disorder, palsy, high blood pressure, neuralgia, and asthma. Such a pharmacological action of a pine needle is achieved by functional substances, such as an essential oil component, protein, vitamin A, vitamin C, vitamin K, vitamin P (routine), phosphorous, iron content, ferment, tannin, chlorophy, a bitter substance, and flavonoid contained in a pine needle. In particular, vitamin P (routine) has an excellent effect of accelerating blood circulation and preventing high blood pressure and aging. Furthermore, the volatile essential oil of a pine needle functions to remove fatigue upon forest therapy. Pine needle extractions are added to herbal medicine mixture extracts corresponding to a moxibustion liquid, and thus strengthens the human body immunity function and performs an anti-inflamatory action and a variety of types of useful biological active actions.

*Cirsium japonicum* is a perennial herb of asteraceae and grows wild in mountains and fields in various places of Korea. *Cirsium japonicum* is called the root of *Cirsium japonicum*, that is, pharmaceuticals, and has been known to have effects, such as blood cooling stanching, blood circulation detoxification, and anti-inflammation. In particular, it has been known that *Cirsium japonicum* has an excellent stanching action. A major component having such a stanching action is a component called pectolinarin. It has been reported that a bleeding time was reduced in a capacity-dependent manner in experiments using experimental rats. Furthermore, it has also been known that *Cirsium japonicum* has anticancer and immunity enhancement effects because it has activity for accelerating the proliferation of a lymphocyte, increasing the activity of an NK cell, and suppressing a tumor. In addition, it has been known that *Cirsium japonicum* is used for the treatment of symptoms, such as a cold, a whooping cough, the inflammation of the intestines, nephritis, the vomiting of blood, bloody urine, bloody excrement or that bleeding is not stopped after childbirth or leucorrhea and a tumor. Furthermore, components including various biological activities as described above are separated and purified from *Cirsium japonicum*. Biological activity components of *Cirsium japonicum* that have been known so far include essential oil compounds such as aplotaxene, dihydroaplotaxene, caryophyllene, thujopsene, and α-himachalene, triterpene compounds such as α-amyrin and β-amyrin, and polyacetylene compounds. *Cirsium japonicum* extractions are added to herbal medicine mixture extracts corresponding to a moxibustion liquid and strengthens the human body immunity function and has an anti-inflammatory action and a variety of types of useful biological active actions.

*Plantago asiatica* is a *plantago* species plant belonging to *plantago* inaceae and a medicinal herb that grows wild in East Asia, such as Korea, China, and Japan, and Central Asia. *Plantago asiatica* has a strong life force as much as weeds at the roadside and an excellent propagation power. *Plantago asiatica* dried before *plantago* when a flower blooms is called a *plantago* herb, and a seed thereof is called a *plantago* seed. In an herbal medicine, *Plantago asiatica* has been widely used in nephritis, cystitis, and urethritis as a strong diuretic. *Plantago asiatica* contains a large amount of inorganic matters, protein, vitamin species and polysaccharide, and it has been known that such components are concerned in an anti-inflamatory action. In particular, a *plantago* seed has been importantly used as a cough remedy not containing saponin and has also been known to have an effect in chronic bronchitis. Furthermore, a *plantago* seed has been used as a mucilage agent in Europe and U.S.A., and is being used as a geriatric diseases treatment agent, such as chronic hepatitis and arteriosclerosis, because it has recently been recognized to have a lipotropic action. Major biological activity components of *Plantago asiatica* include iridoid, glycoside, phosphorous, aucubin, plantaglucoside, and a variety of types of sterol species which are found in the leaves of *plantago asiatica*. It has been known that a seed contains mucilage, adenine, choline, and a variety of types of fatty acids. Meanwhile, it has been researched and reported that aucubin separated from $H_2$ subdividing of seed and leaves, that is, one of major biological activity components of *plantago asiatica*, suppresses ribonucleic acid biosynthesis of an animal cancer cell. It has also been reported that aucubin has other important actions, such as an anti-bacteria action, a choleresis action, a relaxation action, a hepatotoxicity defense action, and a blood pressure drop action. Furthermore, it has been checked that as the results of research regarding an anticancer effect using various types of medicals prepared including *Plantago asiatica*, the generation of active oxygen within the liver, and an anti-oxidation enzyme system control effect, *Plantago asiatica* has a carcinogens suppression effect of suppressing the activities of B(A)P, 2-AE or TRP-P-1, that is, a cancer-causing agent, by 80% or more. Furthermore, it has been checked that phenylethanoid glycoside compounds included in *Plantago asiatica* include plantasioside, orobanchoside, hellicoside, plantamajoside, isoplantamajoside, acetoside, and 3,4-DPCG(3,4-dihydroxyphenethyl alcohol-6-0-caffeoyl-β-Dglucoside) and flavone glucoside compounds included in *Plantago asiatica* include separated plantaginin. It has been known that such glucoside components control the action of ferments, such as cyclic AMP phosphodiesterase, 5-lipoxygenase, and lens aldose reductage. *Plantago asiatica* is added to a bioactive substance composite added to a mugwort liquid according to the present invention, and strengthens the human body immunity function and has a variety of types of useful biological active actions. *Plantago asiatica* extractions are added to herbal medicine mixture extracts corresponding to a moxibustion liquid, thus strengthening the human body immunity function and having an anti-inflammatory action and a variety of types of useful biological active actions.

The skin contact portion 27 is provided on the outer circumference surface of the lower base 20. The skin contact portion 27 forms the indirect heating space that provides a heating effect to portions around an acupuncture point to be treated by surrounding the funnel portion 21, and functions to isolate the bottom of the funnel portion 21 from the skin. The skin contact portion 27 includes an inner container 27a forming the indirect heating space by surrounding the funnel portion 21 and an outer container 27b surrounding the inner container 27a and having a bottom thereof actually come into contact with the skin.

The inner container 27a may be fabricated using various materials and shapes, but is fabricated to have a metallic cylindrical shape. The outer container 27b may be fabricated using various materials and shapes, but is made of a heat-resistant rubber material. The outer container 27b is further extended to the upper and lower sides compared to the inner container 27a so that it closely adheres to the skin and the upper main body 10 is inserted into the lower base 20 and coupled thereto.

In particular, locations portions of 0° and 180° and location portions 90° and 270° at the bottom corner of the outer container 27b are formed to have a smooth curve having a height difference of 1 mm to 5 mm, preferably 2 mm so that a contact force with the skin is improved and the outer container 27b rarely slides.

Furthermore, the outer container 27b includes 1 to 25 parts by weight of a far-infrared emission device selected from the group consisting of 100 parts by weight of a heat-resistant rubber, sericite, illite, mica, and white mica, and thus provides an effect attributable to far-infrared in addition to moxibustion treatment and thermal treatment effects. In this case, the amount of 15 to 25 parts by weight of the far-infrared emission device is mixed with 100 parts by weight of the heat-resistant rubber.

Far-infrared emissivity and radiation energy were measured at a temperature of 40° C. with respect to the outer container 27b fabricated by adding a total amount of 15 parts by weight of sericite and illite, each having 7.5 parts by weight, to 100 parts by weight of the heat-resistant rubber and shown in Table 1. In this case, the results of the far-infrared emissivity and radiation energy compared to a black body were measured using an FT-IR spectrometer that is ultraviolet spectrophotometry.

TABLE 1

| TEST ITEMS | | TEST RESULTS | TEST METHOD |
| --- | --- | --- | --- |
| Far-infrared emission (40° C.) | Emissivity (5 to 20 m) | 0.901 | KCIM-FIR 1005 |
| | Radiation energy (w/m$^2$) | 3.62 × 10$^2$ | |

As may be seen from Table 1, emissivity and radiation energy of far-infrared emitted by the outer container 27b including the far-infrared emission device are very high. It may be seen that a moxibustion therapy effect can provide even a far-infrared effect in addition to a heating therapy effect.

Furthermore, the aforementioned upper main body 10 is detachably coupled to the aforementioned lower base 20. For the strong coupling of the upper main body 10 and the lower base 20, coupling protrusions 19 are protruded from the bottom surface of the upper main body 10, and the coupling grooves 29 to which the coupling protrusions 19 are detachably coupled are formed at the top surface of the lower base 20. In some embodiments, coupling grooves may be depressed in the bottom surface of the upper main body 10, and coupling protrusions detachably coupled to the coupling grooves may be protruded from the top surface of the lower base 20.

Furthermore, the aforementioned lower base 20 includes the temperature sensor 40. The temperature sensor 40 measures a temperature of a portion to be treated under the funnel portion 21 and transfers the measured temperature to the control circuit unit 12 so that the temperature of the portion to be treated can be monitored. The temperature sensor 40 is located on the end of a support 41 that is horizontally extended from a middle location with respect to the skin under the funnel portion 21. The end of the support 41 on which the temperature sensor 40 is located is spaced 1 to 5 mm from the lower center of the funnel portion 21 to the outside in order not to hinder heat concentrated by the funnel portion 21 from being directly delivered to a corresponding acupuncture point to be treated.

The temperature sensor 40 includes a Resistance Temperature Detector (RTD). The resistance temperature detector forming the temperature sensor 40 is made of one of platinum, nickel, copper, an iron-nickel alloy, a copper-nickel alloy, and a copper-iron alloy.

The temperature sensor 40 adopts an RTD method. In general, electric resistance of metal increases or decreases depending on a change of temperature, and electric resistance and a temperature have a constant relation. An instrument for measuring a temperature using this principle is a resistance thermometer, and the wire materials of the resistance temperature detector include platinum, copper, nickel, etc. Platinum is most widely used because it has a very correct temperature relation and excellent stability and reappearance and allows a uniform wire to be fabricated. An available temperature range is −200 to 500° C. The resistance temperature detector may be made of nickel, copper, a nickel-iron alloy or a nickel-copper alloy in addition to platinum.

The resistance temperature detector indicates resistance versus temperature output and requires only about 1 mA for driving because it is manual equipment. Furthermore, the resistance temperature detector has linearity and is stable. The resistance temperature detector made of platinum is preferred for accuracy, but the resistance temperature detector made of a different material may be used by taking a cost into consideration.

In the portable electronic moxibustion therapy device 1 according to an embodiment of the present invention, a temperature of a portion to be treated according to heat generated from the heat generation unit 13 may be set and controlled to one of a first step having a temperature range of 40 to 45° C., a second step having a temperature range of 45 to 50° C., and a third step having a temperature range of 50 to 60° C. based on the temperature monitoring of the temperature sensor 40 and the control circuit unit 12. Such operation temperature mode of the first step to the third step is set by a manipulation of the manipulation unit 14. In this case, the first step having the temperature range of 40 to 45° C. and the second step having the temperature range of 45 to 50° C. may also be used by common users due to the addition of a treatment time timer. In contrast, three-step high-temperature mode having the temperature range of 50 to 60° C. may have an abnormal change of a skin tissue if a specific time is exceeded. If three-step high-temperature mode is used by a common user, there is a danger of a burn. Accordingly, three-step high-temperature mode is configured to be applied if treatment only in a medical institution including an herb doctor is required.

In the portable electronic moxibustion therapy device 1 according to an embodiment of the present invention, the battery 11 and the control circuit unit 12 are configured to standardize and provide a minimum treatment time so that the minimum treatment time maintains 15 to 30 minutes, more preferably, 18 to 20 minutes by considering that an acupuncture treatment effect appears only when treatment is performed for about 18 minutes in accordance with a preferred embodiment of the present invention, that is, clinical tests and an experience rule. Furthermore, the capacity of the battery 11 is provided to maintain 25 to 30 minutes.

An adhesive pad 50 is coupled to the bottom of the aforementioned lower base 20, in particular, the lower periphery of the outer container 27b. The adhesive pad 50 directly adheres to the skin and attaches and fixes the lower base 20 to the skin. The adhesive pad 50 is formed to have a structure in which release paper is attached to the top and bottom surfaces of non-woven fabric or a pad having a sense of volume and having adhesives coated on both sides thereof.

The adhesive pad 50 is fabricated by forming non-woven fabric or a medical pad having a sense of volume and having adhesives coated on both sides thereof in a polygonal shape or a circle and then forming a through hole having a diameter smaller than the diameter of the lower part of the skin contact portion 27 of the lower base 20 at the center of the non-woven fabric or medical pad. Release paper having a through hole formed at the center thereof is attached to the top and bottom surfaces of the adhesive pad 50.

In particular, a plurality of cuts, in particular, two cuts are formed at an interval of 180 degrees in the circumference of the through hole of the adhesive pad 50. A portion having a smaller diameter than the lower part of the skin contact portion 27 of the lower base 20 is separated by the cuts and attached to the lower circumference of the skin contact portion 27 of the lower base 20, and the remaining portions are attached to the circumference of the skin of an acupuncture point to be treated in order to prevent heat and moisture within the lower base 20 from leaking to the outside of a portion to be treated.

Various adhesive means, such as a rubber ring and a string, may be provided in the aforementioned lower base 20 depending on an adhesive portion instead of the aforementioned adhesive pad 50.

In the case of the aforementioned portable electronic moxibustion therapy device 1 according to the present invention, a user can conveniently carry the portable electronic moxibustion therapy device after it is charged, can attach it to a corresponding acupuncture point without any time and place limits, and thus can have a traditional moxibustion therapy effect. Furthermore, the aforementioned portable electronic moxibustion therapy device 1 can also be easily used in a medical institution.

Furthermore, in the case of the portable electronic moxibustion therapy device 1 according to the present invention, a moxibustion therapy effect can be maximized because a heat stimulus can be directly applied to a corresponding acupuncture point to be treated intensively in a close state by means of the funnel portion 21 that concentrates heat on the corresponding acupuncture point without having a direct contact with the corresponding acupuncture point and at the same time, an indirect thermal effect continues to be applied to a surrounding acupuncture point and portions around the corresponding acupuncture point to by means of the heat dissipation hole 22 of the funnel portion 21 and the skin contact portion 27. Furthermore, a moxibustion therapy effect can be maximized because moxa extracts or a moxibustion liquid including the moxa extracts penetrate the skin through a liquefaction state and a vaporization method wet type contact, thereby being capable of maximizing a pharmacological action.

Furthermore, the portable electronic moxibustion therapy device 1 according to the present invention can be generalized as a medical instrument because a heat stimulus temperature and a heat stimulus time can be standardized and provided for each step through the temperature monitoring of the temperature sensor 40. Furthermore, the portable electronic moxibustion therapy device 1 can be effectively used depending on symptoms in a specialized medical institution as well as by a common user because it is configured to select a heat stimulus temperature for each step, if necessary, and to perform treatment.

Furthermore, in the case of the portable electronic moxibustion therapy device 1 according to the present invention, the upper main body 10 including a simple circuit and the lower base 20 in which a moxibustion liquid is vaporized are separated, and the portable electronic moxibustion therapy device 1 is configured so that a moxibustion liquid of a liquid state is injected according to an automatic injection method using the cartridge or an external manual injection method using a spuit. In particular, the popularization of the portable electronic moxibustion therapy device can be accelerated because the external manual injection method can be fabricated and sold at a low price, and medical expenses can be significantly reduced if anyone can easily use the portable electronic moxibustion therapy device through such popularization.

A moxibustion liquid state container and an injection spuit can be together provided as auxiliary equipment so that anyone can easily use the external manual injection method of a moxibustion liquid which can be implemented at a lower cost.

INDUSTRIAL APPLICABILITY

The present invention may be applied to a moxibustion treatment device which allows traditional moxibustion treatment while it is conveniently carried by a user after it is charged.

The invention claimed is:

1. A portable electronic moxibustion therapy device, comprising:
   an upper main body in which a battery and a control circuit unit are provided on an upper side of the upper main body, a heat generation unit for generating heat under a control of the control circuit unit is protruded from the upper main body at a bottom of the upper main body, and a manipulation unit and a display unit are provided on an outer surface of the upper main body; and
   a lower base which is coupled to the bottom of the upper main body, has the heat generation unit inserted into a center of the lower base and coupled to the lower base, and comprises a funnel portion which concentrates heat transferred from the heat generation unit on one point at a bottom of the funnel portion and has at least one guide groove formed along an outer circumference surface of the funnel portion, at least one moxibustion liquid injection pipe which is provided outside the funnel portion and injects a moxibustion liquid so that the moxibustion liquid is vaporized along the at least one guide groove, and a skin contact portion which is provided on an outer circumference surface of the lower base, forms an indirect heating space by surrounding the funnel portion, and isolates the bottom of the funnel portion from a skin.

2. The portable electronic moxibustion therapy device of claim 1, wherein:
   a coupling protrusion is protruded and formed on a bottom surface of the upper main body, and
   a coupling groove to which the coupling protrusion is detachably coupled is formed on a top surface of the lower base.

3. The portable electronic moxibustion therapy device of claim 1, wherein a charging jack connection hole to which a charging jack of a charging cable for charging the battery is connected is provided on one side of the upper main body.

4. The portable electronic moxibustion therapy device of claim 1, wherein the moxibustion liquid is manually injected through the moxibustion liquid injection pipe.

5. The portable electronic moxibustion therapy device of claim 1, wherein:
   a cartridge coupling hole communicating with the moxibustion liquid injection pipe by a connection pipe is formed on a top surface of the upper main body so that the moxibustion liquid is automatically injected into the moxibustion liquid injection pipe, and
   a moxibustion liquid cartridge filled with the moxibustion liquid is detachably coupled to the cartridge coupling hole.

6. The portable electronic moxibustion therapy device of claim 1, wherein the moxibustion liquid comprises moxa extracts.

7. The portable electronic moxibustion therapy device of claim 1, wherein the moxibustion liquid comprises 100 parts by weight of moxa extracts and 1 to 10 parts by weight of a microbial cultivated liquid cultivated using one or more of yeast fungus, lactobacilli, photosynthesis bacteria, aspergilli, and actinomicetes ray fungi using a liquid state medium at room temperature.

8. The portable electronic moxibustion therapy device of claim 1, wherein the moxibustion liquid comprises 100 parts by weight of moxa extracts and 1 to 40 parts by weight of additional extracts including at least one selected from a group consisting of bitter gourd extracts, dandelion extracts, pine needle extracts, *Curcuma longa* L. extracts, *Cirsium japonicum* extracts, and *Plantago asiatica* extracts.

9. The portable electronic moxibustion therapy device of claim 1, wherein the moxibustion liquid comprises 100 parts by weight of moxa extracts, 1 to 40 parts by weight of additional extracts including at least one selected from a group consisting of bitter gourd extracts, dandelion extracts, pine needle extracts, *Curcuma longa* L. extracts, *Cirsium japonicum* extracts and a *Plantago asiatica* extracts, and 1 to 10 parts by weight of a microbial cultivated liquid cultivated using one or more of yeast fungus, lactobacilli, photosynthesis bacteria, aspergilli, and actinomicetes ray fungi using a liquid state medium at room temperature.

10. The portable electronic moxibustion therapy device of claim 1, wherein:

two guide grooves comprising the at least one guide groove are formed, the two guide grooves start from both sides on an upper part of the funnel portion, downward make a turn around the outer circumference surface of the funnel portion by 360 degrees, and reach the bottom of the funnel portion, and two moxibustion liquid injection pipes comprising the at least one moxibustion liquid injection pipe are formed and connected to tops of the two guide grooves, respectively.

11. The portable electronic moxibustion therapy device of claim 1, wherein a heat dissipation hole is formed to penetrate the funnel portion.

12. The portable electronic moxibustion therapy device of claim 1, wherein a temperature sensor for measuring a temperature of a portion to be treated and transferring the measured temperature to the control circuit unit is provided at the bottom of the funnel portion.

13. The portable electronic moxibustion therapy device of claim 12, wherein the temperature sensor comprises a resistance temperature detector (RTD).

14. The portable electronic moxibustion therapy device of claim 13, wherein the resistance temperature detector is made of one of platinum, nickel, copper, an iron-nickel alloy, a copper-nickel alloy, and a copper-iron alloy.

15. The portable electronic moxibustion therapy device of claim 12, wherein a temperature of a portion to be treated according to heat generated from the heat generation unit of the upper main body is set to one of a first step having a temperature range of 40 to 45° C., a second step having a temperature range of 45 to 50° C., and a third step having a temperature range of 50 to 60° C. in response to a manipulation of the manipulation unit.

16. The portable electronic moxibustion therapy device of claim 12, wherein:

the temperature sensor is located on an end of a support horizontally extended from a middle location with respect to the skin under the funnel portion, and the end of the support on which the temperature sensor is located is spaced 1 to 5 mm from a lower center of the funnel portion to an outside.

17. The portable electronic moxibustion therapy device of claim 1, wherein the skin contact portion of the lower base comprises:

an inner container forming the indirect heating space by surrounding the funnel portion, and an outer container surrounding the inner container and made of a heat-resistant rubber material, wherein the outer container is more extended to upper and lower sides than the inner container and has a bottom actually come into contact with the skin.

18. The portable electronic moxibustion therapy device of claim 17, wherein:

the outer container has a cylinder form, and locations portions of 0° and 180° and location portions 90° and 270° at a bottom corner of the outer container are formed to have a smooth curve having a height difference of 2 mm so that a contact force with a skin is improved and the bottom corner rarely slides.

19. The portable electronic moxibustion therapy device of claim 17, wherein the outer container comprises 1 to 25 parts by weight of a far-infrared emission device selected from a group consisting of 100 parts by weight of a heat-resistant rubber, sericite, illite, mica, and white mica.

20. The portable electronic moxibustion therapy device of claim 19, wherein an amount of 15 to 25 parts by weight of the far-infrared emission device is mixed with 100 parts by weight of the heat-resistant rubber.

21. The portable electronic moxibustion therapy device of claim 1, further comprising an adhesive pad coupled to a lower circumference of the lower base and directly attached to the skin, for attaching the lower base to surrounding portions of a skin of a portion to be treated.

22. The portable electronic moxibustion therapy device of claim 21, wherein:

the adhesive pad comprises non-woven fabric or a pad having adhesives coated on both sides of the non-woven fabric or pad and having a through hole of a diameter smaller than a diameter of a lower part of the skin contact portion of the lower base at a center of the non-woven fabric or pad, release paper is attached to top and bottom surfaces of the adhesive pad, a plurality of cuts is formed in a circumference of the through hole of the adhesive pad, a portion having a smaller diameter than the lower part of the skin contact portion of the lower base is separated by the cuts and attached to the lower circumference of the skin contact portion of the lower base, and remaining portions are attached to the circumference of the skin of an acupuncture point to be treated so that heat and moisture within the lower base is prevented from leaking to an outside of a portion to be treated.

* * * * *